(12) United States Patent
Lohsomboon

(10) Patent No.: US 6,561,125 B1
(45) Date of Patent: May 13, 2003

(54) INSECT STORAGE AND SHIPPING CONTAINER

(76) Inventor: Vesspong Lohsomboon, 20141 Lanark St., Canoga Park, CA (US) 91306

( * ) Notice: Subject to any disclaimer, the term of this patent is extended or adjusted under 35 U.S.C. 154(b) by 0 days.

(21) Appl. No.: 10/099,059

(22) Filed: Mar. 15, 2002

(51) Int. Cl.[7] .............................................. A01K 29/00
(52) U.S. Cl. ...................................... 119/6.5; 119/416
(58) Field of Search ......................... 119/6.5, 416, 417, 119/452, 453, 454; 43/54.1, 55

(56) References Cited

U.S. PATENT DOCUMENTS

| | | | |
|---|---|---|---|
| 3,345,974 A | * 10/1967 | Phillips et al. | 119/6.5 X |
| 4,811,693 A | * 3/1989 | Müller | 119/416 |
| 5,398,642 A | * 3/1995 | Harwich | 119/6.5 |
| 5,586,406 A | * 12/1996 | Lin et al. | 43/55 |
| 5,630,374 A | 5/1997 | Cunningham | 119/6.5 |

* cited by examiner

*Primary Examiner*—Robert P. Swiatek
(74) *Attorney, Agent, or Firm*—Jack C. Munro

(57) ABSTRACT

An insect storage and shipping container which takes the form of a transparent vessel within which is mounted a pair of spaced apart panels. The panels can be used to hold food in cake form. The panels also include roughened surfaces in order to increase the amount of available space within the vessel for the insects to maneuver about. The lid of the vessel includes spacers which permit stacking of the containers in a manner to keep the air holes contained within the lid open. A grate may be installed in conjunction with the panels with the grate normally located a short distance from the floor of the vessel.

5 Claims, 3 Drawing Sheets

INSECT STORAGE AND SHIPPING CONTAINER

BACKGROUND OF THE INVENTION

1. Field of the Invention

The present invention is directed to storage and shipping containers and more particularly to a storage and shipping container for insects where the insects are to be used for food or bait.

2. Description of the Related Art

Some insects are genetically bred to be used as food or bait. Some insects are fed to fish, frogs, other amphibians, tarantulas, praying mantises, scorpions, spiders, and so forth. Common insects that are produced and sold as food and bait for fish are grey crickets and fruit flies. Fruit flies are used as food for invertebrates, reptiles and amphibians.

From where the crickets and fruit flies are produced, such needs to be made available to the consumer. There are aquarium businesses and bait shops that sell both crickets and fruit flies. It is common for the crickets and fruit flies to be sent in mass in some type of shipping container. The retail merchant is to extract an approximate number of the crickets and place such in some kind of container, usually a paper pot, for the consumer to take such to his home, business or fishing area to thereby utilize the insects.

Food and water have to be included with the insects as they are shipped or, of course, the insects will die. It is common that, in conjunction with crickets, a small quantity of a vegetable is placed within the shipping container. The crickets walk all over the food leaving feci deposits which is undesirable for the health of the crickets and can actually result in the crickets dying prematurely.

It is normal that when shipping crickets to a destination about ten percent die. This is undesirable as dead crickets are not saleable. It is desirable to utilize some form of shipping container where it is normal that less than five percent of the crickets die.

The overall normal procedure for selling of insects requires direct involvement by the retail merchant in order to obtain a desired quantity of insects placed within a box-type container and given to the consumer. It would be desirable to have some kind of container that could be manufactured with this container being designed to hold an approximate number of insects and utilized for shipping to the retail merchant. Then the container only needs to be purchased by the user with the user then dispensing the insects directly from the container. No contact by any human being with the insects is required.

SUMMARY OF THE INVENTION

An insect storage and shipping container which comprises a vessel which has an internal chamber with the vessel having a floor and an enclosing sidewall. Also, there is an open top edge. There is mounted within the internal chamber of the vessel a panel mounting means which is mounted on both sidewall and the floor. Spaced-apart panels are removably mounted in conjunction with the panel mounting means with each of the panels having a vertical groove. A food cake is designed to be placed between the vertical grooves which functions as a secure location mount for the food cake.

A further embodiment of the present invention is where the basic embodiment is modified by the vessel being cylindrical.

A further embodiment of the present invention is where the first basic embodiment is modified by the sidewall of the vessel being transparent.

A further embodiment of the present invention is where the first basic embodiment is modified by each of the panels including a mass of ridges in order to provide surfaces upon which the insects can walk.

A further embodiment of the present invention is where the first basic embodiment is modified by there being incorporated a separate grate in conjunction with the panels. The grate is to be slidingly mounted on the panels.

A further embodiment of the present invention is where the first basic embodiment is modified by there being included a lid which includes air holes, with the lid to be mounted on the vessel and function to close the access opening into the internal chamber at the top edge. Exteriorly mounted on the lid are a series of spacers which permits stacking of the containers and not closing of the air holes when they are stacked.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE INVENTION

Figure 1:
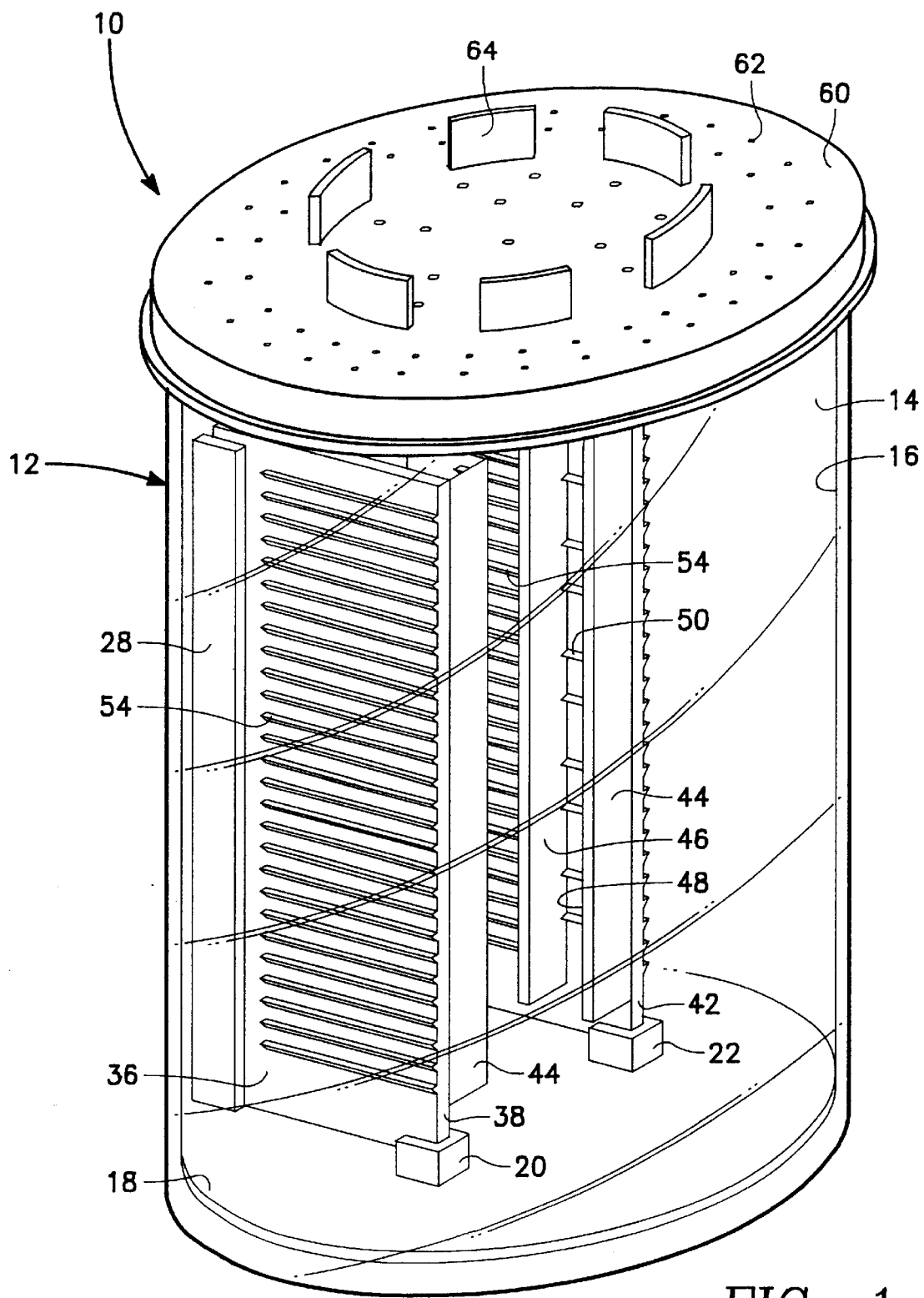
FIG. 1 is an exterior isometric view of the insect storage and shipping container of the present invention which is designed primarily to be used for crickets.
Figure 2:
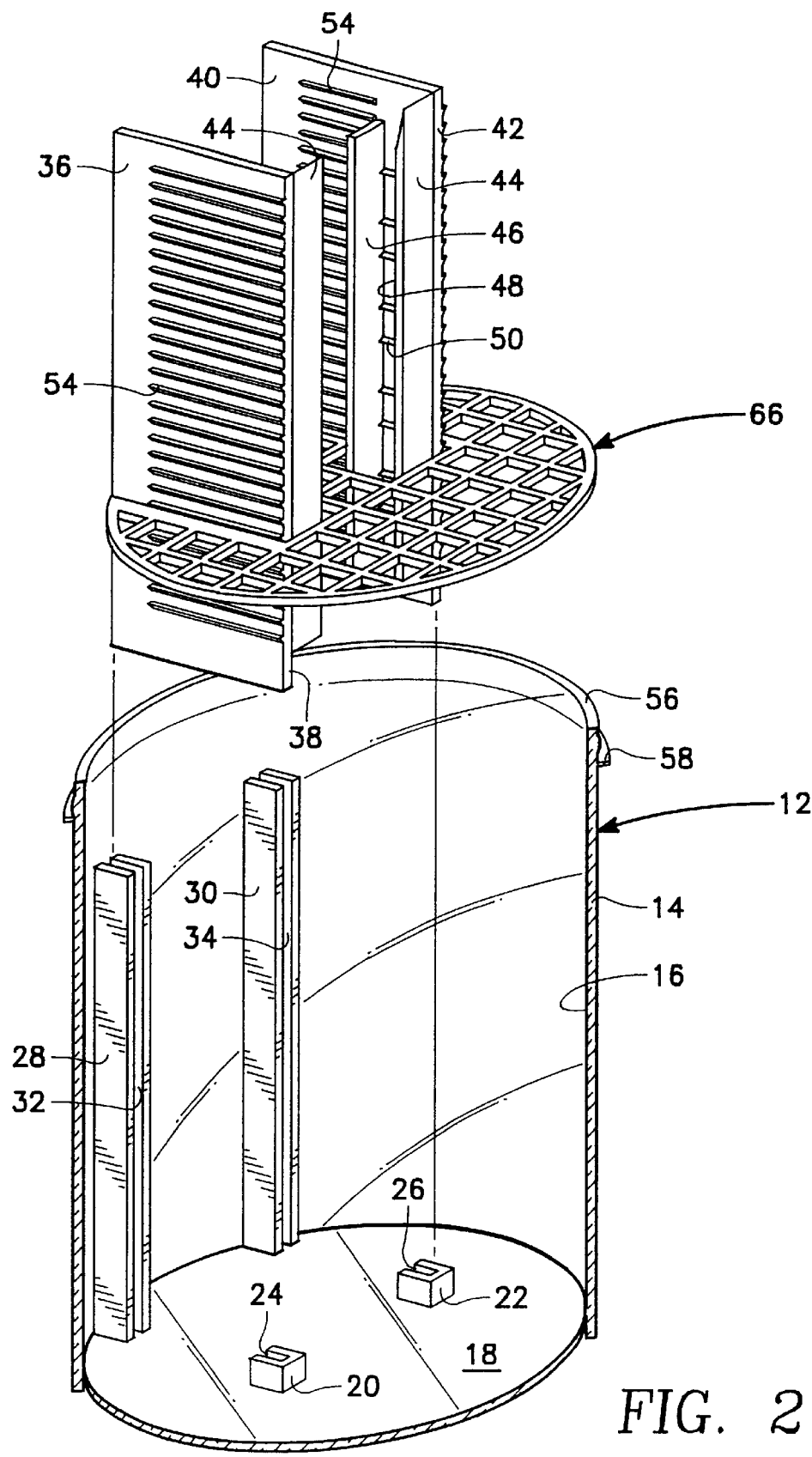
FIG. 2 is a cut-away, exploded, isometric view of the insect storage and shipping container of the present invention also showing the addition of a removable grate which will permit the container to be used for fruit flies.

Referring particularly to the drawings, there is shown in FIG. 1 the insect storage and shipping container 10 of this invention. The container 10 utilizes a vessel 12 which has a transparent enclosing sidewall 14. Typically, the sidewall 14 will be constructed of plastic sheet material. The sidewall 14 encloses an internal chamber 16. Internal chamber 16 is closed at the bottom by means of a floor 18 which is fixedly secured to the lower end of the sidewall 14.

Mounted on the floor 18 is part of a panel mounting structure in the form of a pair of notched blocks 20 and 22. The notched blocks 20 and 22 are located spaced apart. Notched block 20 includes a notch 24. Notched block 22 includes a notch 26. Fixedly mounted to the interior of the sidewall 14 are a pair of spaced apart guide rails 28 and 30. Guide rail 28 includes a longitudinal through slot 32. Guide rail 30 includes a similar longitudinal through slot 34. Guide rail 28 is in alignment with the block 20. Guide rail 30 is in alignment with the block 22.

A thin sheet material panel 36 is to be slid within the slot 32 until the panel 36 rests on the floor 18. The forward edge 38 of the panel 36 will fit within the notch 24. A panel 40, identical to panel 36 but reversely positioned in a mirror image relationship relative to panel 36, is to be slid within the slot 34 where its lower edge will rest on the floor 18 and its forward edge 42 will fit within the notch 26 of the block 22. Panels 36 and 40 function as insect climbing structures so the insects can move about thereon. Each of the panels 36 and 40 has mounted thereon a pair of vertical strips 44 and 46. Formed between the strips 44 and 46 is a groove 48. Fixed on the surface of each of the panels 36 and 40 and located within their respective groove 48 are a series of spaced apart protuberances 50. A food and water cake 52 is to be placed in a snug manner between aligned grooves 48 of each of the panels 36 and 40. The protuberances 50 will function to help secure in position the cake 52. Typical composition for the food and water cake 52 will be a quantity of a gel, a small amount of sodium benzoate, a small amount of potassium sorbet and about fifty percent water in combination with the food that is to be eaten by the insects. Typically, the food will include a soybean meal, cracked corn, cracked milo, ground milo, wheat bran, meat and bone meal, as well as many other ingredients.

It is to be noted that the panel 36 has formed on both its inner and outer sides a series of horizontal ridges 54. The ridges 54 provide an uneven surface on the panels 36 and 40 which will permit the insects to climb up and down the panels 36 and 40. The insects will not be able to climb on the inside surface of the sidewall 14 for the mere fact that it is too smooth for them to do so. However, it is desirable to include as much area within the internal chamber 16 as possible in order to permit the insects to have as much area on which to maneuver which helps to keep the insects from stacking up on each other. It is for this reason that the ridges 54 have been formed within the panels 36 and 40.

Mounted on the exterior surface of the sidewall 14 adjacent the top edge 56 is an annular flange 58. The annular flange 58 is to facilitate engagement with a lid 60. The lid 60 includes a mass of air holes 62 whose function is to permit air to be conducted within the confines of the internal chamber 16 to be breathed by the insects. Also mounted on the lid 60 are a plurality of spaced apart spacers 64. There are six in number of the spacers 64. However, it is considered that this number could be increased or decreased without departing from the scope of this invention. Also, instead of having a plurality of separate members 64, there could be one continuous ring. Basically, each spacer 64 comprises a raised, narrow block of material.

Figures 3, 4:
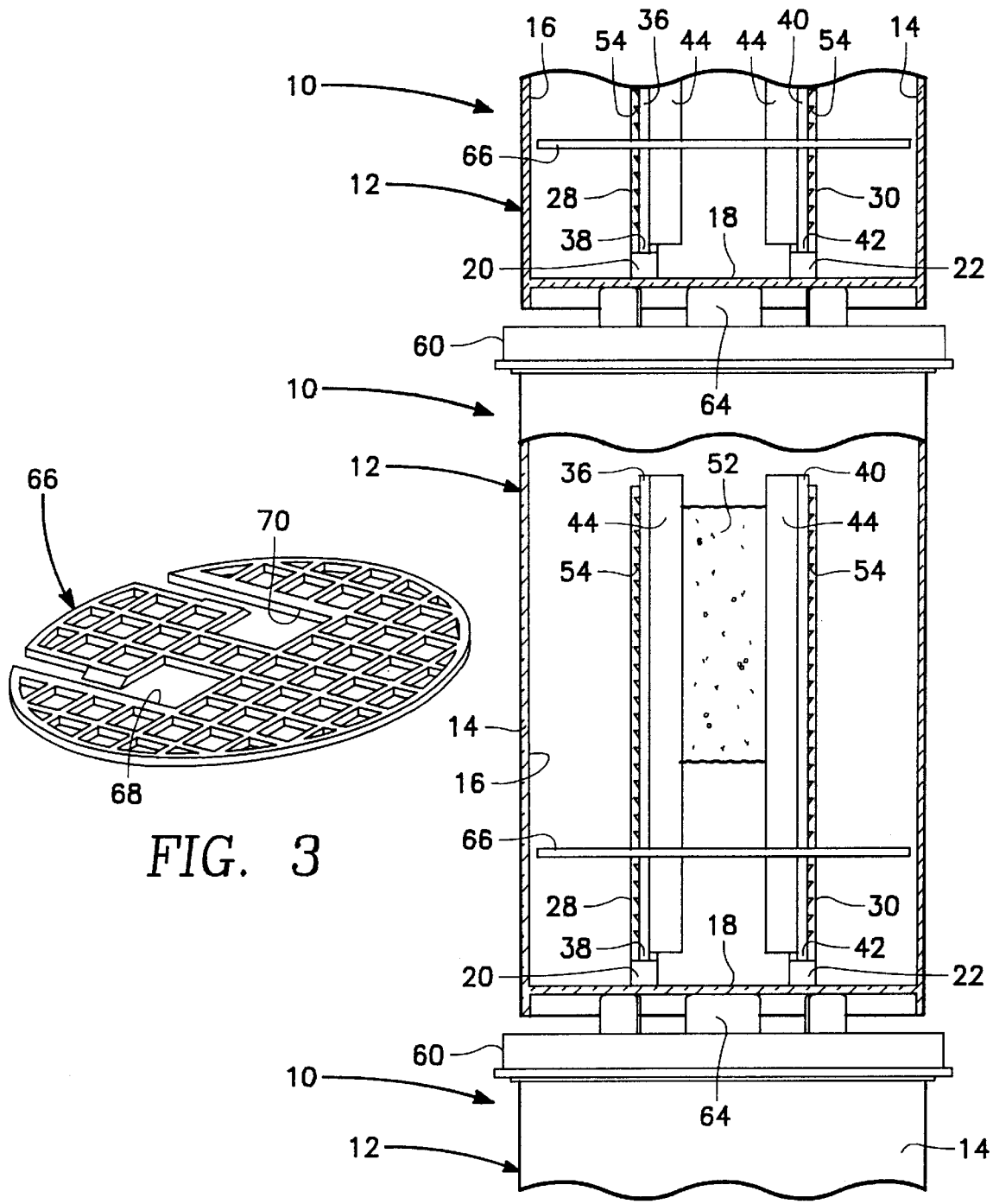
FIG. 3 is an isometric view of the grate that is utilized for fruit flies.
FIG. 4 is a partially cut-away view of a plurality of the insect storage and shipping containers of the present invention showing such in a stacked configuration.

After the desired number of insects have been supplied with the internal chamber 16, such as approximately forty crickets, the lid 60 is fixedly installed in conjunction with the flange 58 forming a tight fit with the sidewall 14. It is to be understood that the panels 36 and 40 have been previously installed in place and the food cake 52 also properly installed between the panels 36 and 40. The container 10 is now ready to be shipped to a desired location, and once it reaches its desired location is able to be purchased by a consumer with there being no direct handling of the insects by the consumer or by the proprietor of the marketing outlet. The consumer only needs to remove the lid 60, sprinkle a few of the insects into an aquarium or cage or a few of the insects removed for purposes of bait, the lid 60 is then reinstalled in position again closing off the internal chamber 16. Typically, the insects can remain within the container 10 for a period of up to two weeks time. The spacers 64 permit different containers 10 to be stacked on top of one another, as shown in FIG. 4. This stacking will be for purposes of display within a store or will be used in conjunction with shipping. Even when stacked, because of the spacers 64, the air holes 62 are not closed and therefore air will be permitted to enter within the internal chamber 16.

If the container 10 is to be used for a different type of insect, such as a fruit fly, it will normally be desirable to include a grate 66. The grate 66 will be constructed of plastic which includes openings 68 and 70. The opening 68 is to connect with panel 36 and opening 70 is to connect with panel 40. The grate 66 can be slid along the panels 36 and 40, and when a particular desired vertical position has been obtained, the grate 66 will remain in that position. Typically, the grate 66 will be located about one-half an inch to an inch above the floor 18.

What is claimed is:

1. An insect storage and shipping container comprising:
   a vessel having a top edge and an internal chamber surrounded by a sidewall, said vessel having a floor that closes one end of said internal chamber, said internal chamber being open at said top edge; and
   a pair of separate panels mounted in a spaced apart arrangement in conjunction with said sidewall, said panels having a groove arrangement with each panel of said separate panels having a groove, said groove arrangement to receive and hold a food in cake form which locates the food spaced from said bottom and not being subjected to feces dropped by insects.

2. The insect storage and shipping container as defined in claim 1 wherein:
   a lid, said lid being mounted on said top edge to completely enclose said internal chamber, said lid including a mass of air holes, said lid have mounted thereon a plurality of spacers that permit a plurality of said containers to be stacked yet permit the conducting of air through said air holes within said internal chamber.

3. The insect storage and shipping container as defined in claim 1 wherein:
   said sidewall having panel mounting means, said panels removably engaging said panel mounting means.

4. An insect storage and shipping container comprising:
   a vessel having a top edge and an internal chamber surrounded by a sidewall, said vessel having a floor that closes one end of said internal chamber, said internal chamber being open at said top edge;
   an insect climbing structure mounted in conjunction with said sidewall, said climbing structure having a groove arrangement, said groove arrangement adapted to receive and hold a food in cake form which locates the food spaced from said bottom and not being subjected to feces dropped by insects; and
   said climbing structure including a mass of ridges, said ridges to permit the insects to traverse said climbing structure.

5. An insect storage and shipping container comprising:
   a vessel having a top edge and an internal chamber surrounded by a sidewall, said vessel having a floor that closes one end of said internal chamber, said internal chamber being open at said top edge;
   an insect climbing structure mounted in conjunction with said sidewall, said climbing structure having a groove arrangement, said groove arrangement adapted to receive and hold a food in cake form which locates the food spaced from said bottom and not being subjected to feces dropped by insects; and
   a grate slidingly mounted on said climbing structure, said grate to be adjusted to be spaced slightly from said bottom.

* * * * *